US010743997B2

(12) United States Patent
Anapliotis

(10) Patent No.: US 10,743,997 B2
(45) Date of Patent: Aug. 18, 2020

(54) IMPLANTABLE COMPENSATING SLEEVE FOR AN ENDOPROSTHESIS

(71) Applicant: Merete Holding GmbH, Berlin (DE)

(72) Inventor: Emmanuel Anapliotis, Berlin (DE)

(73) Assignee: Merete Holding GmbH, Berlin (DE)

( * ) Notice: Subject to any disclaimer, the term of this patent is extended or adjusted under 35 U.S.C. 154(b) by 155 days.

(21) Appl. No.: 16/081,103

(22) PCT Filed: Mar. 27, 2017

(86) PCT No.: PCT/DE2017/000083
§ 371 (c)(1),
(2) Date: Aug. 30, 2018

(87) PCT Pub. No.: WO2017/167323
PCT Pub. Date: Oct. 5, 2017

(65) Prior Publication Data
US 2019/0021864 A1 Jan. 24, 2019

(30) Foreign Application Priority Data

Mar. 29, 2016 (DE) .................. 10 2016 003 838

(51) Int. Cl.
A61F 2/30 (2006.01)
A61B 17/72 (2006.01)
A61F 2/36 (2006.01)
A61F 2/34 (2006.01)

(52) U.S. Cl.
CPC ...... A61F 2/30907 (2013.01); A61B 17/7283 (2013.01); A61F 2/30734 (2013.01);
(Continued)

(58) Field of Classification Search
CPC ........ A61F 2/30734; A61F 2002/30738; A61F 2002/30919; A61F 2002/30235;
(Continued)

(56) References Cited

U.S. PATENT DOCUMENTS 3,977,398 A 8/1976 Burstein
6,261,289 B1 * 7/2001 Levy .................. A61B 17/7266
606/62

(Continued)

FOREIGN PATENT DOCUMENTS

DE 1805665 5/1970
DE 3909182 8/1990
(Continued)

OTHER PUBLICATIONS

International Search Report, PCT/DE2017/000083, dated Aug. 31, 2017.
Written Opinion, PCT/DE2017/000083, dated Aug. 31, 2017.

*Primary Examiner* — David H Willse
*Assistant Examiner* — Javier G Blanco
(74) *Attorney, Agent, or Firm* — Andrus Intellectual Property Law, LLP

(57) ABSTRACT

An implantable compensating sleeve is for application between a longitudinal implant section of a first implant, and a second implant that encompasses the longitudinal implant section of the first implant. The compensating sleeve has a sheath with a sheath body and a passage, running from the proximal to the distal end of the sheath body, for receiving the longitudinal implant section of the first implant. The sheath body is formed from separate planar and/or rod-shaped compensating elements which are arranged in a ring and aligned in the longitudinal direction of the sheath body. A gap runs from the proximal to the distal end between two adjacent compensating elements. Adjacent compensating elements are interconnected by at least one foldable wire such that they can move relative to one another.

5 Claims, 3 Drawing Sheets

Figure 1:
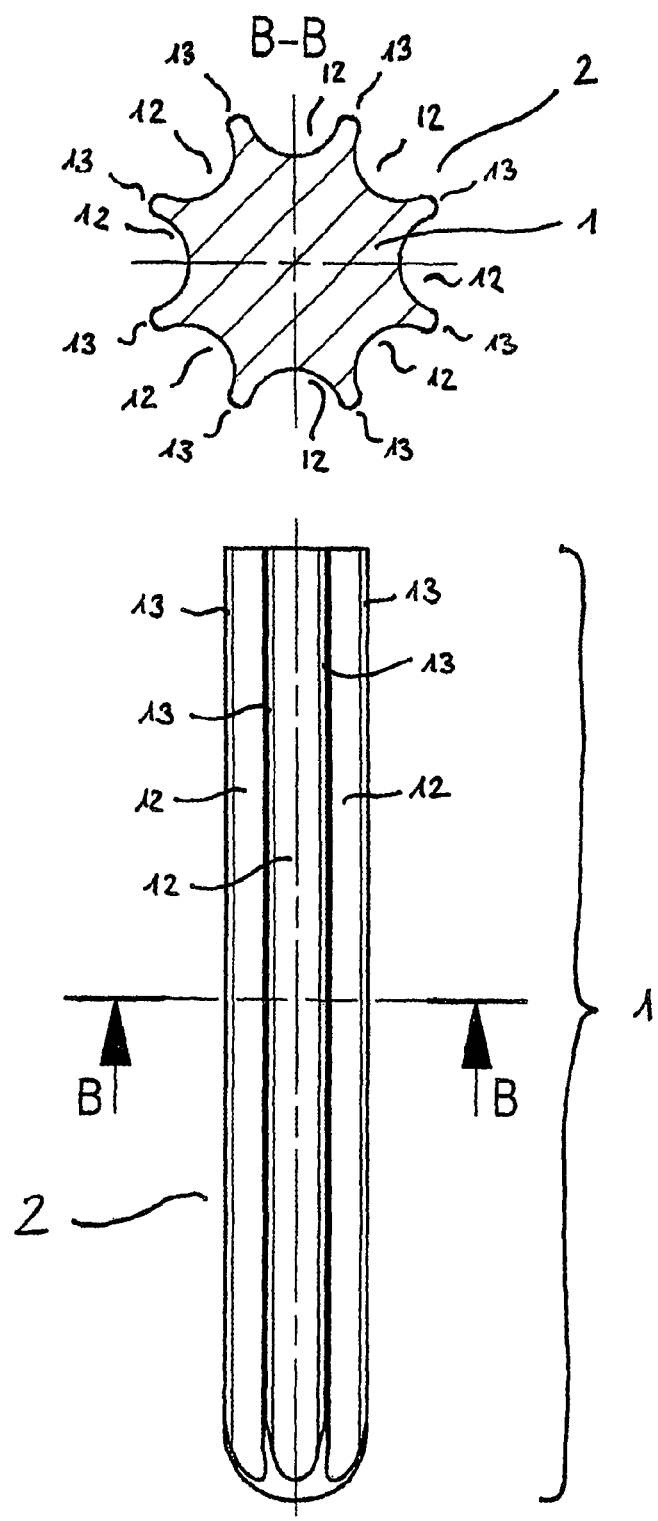

(52) U.S. Cl.
CPC ............ *A61F 2/36* (2013.01); *A61B 17/7233* (2013.01); *A61B 17/7275* (2013.01); *A61F 2002/3069* (2013.01); *A61F 2002/30235* (2013.01); *A61F 2002/30375* (2013.01); *A61F 2002/30462* (2013.01); *A61F 2002/30602* (2013.01); *A61F 2002/30738* (2013.01); *A61F 2002/30884* (2013.01); *A61F 2002/30919* (2013.01); *A61F 2002/3406* (2013.01)

(58) Field of Classification Search
CPC .... A61F 2002/30375; A61F 2002/3069; A61F 2/367; A61F 2/3672; A61F 2/3676; A61B 17/72; A61B 17/7233; A61B 17/7275; A61B 17/7283
See application file for complete search history.

(56) References Cited

U.S. PATENT DOCUMENTS

| | | | |
|---|---|---|---|
| 6,447,543 B1 * | 9/2002 | Studer | A61F 2/2846 623/17.11 |
| 6,783,554 B2 * | 8/2004 | Amara | A61B 17/12022 606/151 |
| 8,668,692 B1 | 3/2014 | Lindvall | |
| 2004/0230193 A1 | 11/2004 | Cheung et al. | |
| 2008/0154314 A1 * | 6/2008 | McDevitt | A61B 17/8095 606/304 |
| 2008/0255560 A1 * | 10/2008 | Myers | A61B 17/7225 606/63 |
| 2008/0269745 A1 * | 10/2008 | Justin | A61B 17/864 606/62 |
| 2011/0238121 A1 | 9/2011 | Watanabe et al. | |
| 2011/0306975 A1 | 12/2011 | Kaikkonen et al. | |
| 2014/0350691 A1 | 11/2014 | Linares | |

FOREIGN PATENT DOCUMENTS

| | | | |
|---|---|---|---|
| DE | 102005054708 | 5/2007 | |
| DE | 102008062226 | 8/2009 | |
| EP | 0761175 | 3/1997 | |
| FR | 2683715 A1 * | 5/1993 | ............ A61F 2/0811 |
| JP | 2955701 | 7/1999 | |

* cited by examiner

IMPLANTABLE COMPENSATING SLEEVE FOR AN ENDOPROSTHESIS

CROSS-REFERENCE TO RELATED APPLICATIONS

This application is the U.S. national stage application of International Application PCT/DE2017/000083, filed Mar. 27, 2017, which international application was published on Oct. 5, 2017 International Publication WO 2017/167323 in the German language. The International Application claims priority of German Patent Application No. 102016003838.1, filed Mar. 29, 2016. The international application and German application are both incorporated herein by reference, in entirety.

This invention concerns an implantable compensating sleeve for an endoprosthesis, in particular for a recumbent endoprosthesis for the intramedullar treatment of a periprosthetic or interprosthetic fracture.

The frequency of occurrence of periprosthetic or interprosthetic fractures is increasing because of the high number of hip and knee prostheses with increasing age of the operated patients.

Periprosthetic fractures are fractures near a prosthesis and often occur as a consequence of a fall. Bad bone quality can also lead to a periprosthetic fracture due to osteoporotic or osteolytic changes.

Interprosthetic fractures occur between two implants and/or prostheses installed in the same bone. One finds interprosthetic fractures most often in the femur between a hip and a knee prosthesis.

Very different forms of therapy are indicated depending on the nature and the course of the fracture, its location with respect to the prosthesis, as well as the in-situ stability of the prosthesis.

It is, in particular, critical for selecting the treatment of the fracture whether the fit of the prosthesis has perhaps loosened up. If the prosthesis remains firmly anchored in the bone, it is often possible to refrain from a revision of the prosthesis.

Angularly stable plate osteosynthesis is the standard method in the treatment of peri- or interprosthetic fractures, which are categorized as type B1 in accordance with the Vancouver classification. However, it is the treatment by way of plate osteosynthesis that often leads to weakening of the prosthetically treated bone, with the formation of predetermined break points in the vicinity of which fractures often occur as a consequence. Depending on the findings, the use of a megaprosthesis for a complete femur replacement can be unavoidable.

If the bone structure does not allow for osteosynthesis, intramedullar stabilization represents an alternative surgical method wherein the defect is bypassed by means of an individually made interposition nail.

Interposition nails offer high stability and are made available in different sizes.

In those instances of fractures of the Vancouver B1 type in which the hip or the knee prosthesis remains firmly anchored in the bone, it is possible to fall back on methods of care wherein the implanted prosthesis can remain in the body. In the case of this surgical method, e.g. to bypass the bone defect in the femur, the shaft of an implanted hip prosthesis is connected with a femur nail, which is inserted distally into the medullary canal via a sleeve-like intermediate module, wherein the shaft can be lengthened mechanically. This procedure offers many advantages. On one hand, the duration and gravity of the surgical procedure can clearly be reduced; on the other hand, one can count on better healing and a higher stability of the prosthetically treated bone along with a simultaneously reduced complication rate.

However, there are only a few modular endoprosthesis systems where the implant and/or prosthesis components are attuned to each other to such an extent that a previously implanted prosthesis can be stably enlarged endoprosthetically in subsequent operations.

The origin of a prosthesis shaft as well as its geometry and condition can often only be determined unequivocally if has been laid open surgically. The surgeon must then decide quickly whether a provided endoprosthesis system would be compatible with the encountered shaft and whether the subsequently implanted endoprosthesis system can be connected with the end of the shaft in a rotationally stable way.

The medical product market offers innumerable hip and knee prostheses, which clearly differ from each other in their configuration and size. The important differences are in particular in the length and the cross-sectional profile of the prosthesis shafts as well as their surface finish. Some prostheses have, among other things, corrugations or grooved profiles extending in the longitudinal direction, which make an intramedullar extension to an endoprosthesis more difficult due to inadequately producible friction between the parts of the prosthesis.

Endoprosthetic connecting system systems wherewith exposed shaft ends can be endoprosthetically lengthened after a periprosthetic fracture are known from the state of the art.

DE 10 2008 062226 A1 discloses an extension of a proximal femur nail. The extension in the form of a retrograde distal femur nail that is introducible into the medullar cavity of the femur has an intake opening at the proximal end, which is slid over the distal end of the proximal femur nail. The locking takes place by way of a locking screw, which is additionally connected to the femur.

U.S. Pat. No. 8,668,692 B1 describes a periprosthetic endoprosthesis system for a previously implanted prosthesis shaft. This endoprosthesis system comprises a connector, which has a three-sided channel extending in the longitudinal direction. The proximal region of this channel is designed to receive the inside-lying end of the shaft and is conical so as to fit the shape of the shaft. The connection between the inside-lying end of the shaft and the conical region of the channel takes place through traction, with or without additional cementing of the end of the shaft. Another implant can be screwed into the distal end region of the channel for endoprosthetic extension.

The disclosure of DE 39 09 182 C1 is moreover referred to as the relevant state of the art.

It is the task of the invention to disclose an implantable auxiliary component for an endoprosthetic extension of an inside-lying implant, by means of which the traction between the inside-lying implant and an endoprosthetic extension can be improved so as to avoid a revision of the inside-lying implant, such that a rotationally stable connection between the inside-lying implant and the endoprosthetic extension can be achieved.

This task is accomplished via an implantable compensating sleeve for an endoprosthesis, which is to be installed between an oblong implant section of a first implant and a second implant which clasps the oblong section of the first implant. The implantable compensating sleeve is designed as a sheath having a body and a lead-through passing to the distal end of the sheath body so as to receive the oblong implant section of the first implant.

The body of the sheath is made of separate planar and rod-shaped compensating elements, which are arranged circularly around the lead-through and are oriented in the longitudinal direction of the sheath body. The compensating elements are arranged at a distance from one another so that a gap passing from distal to proximal extends between two neighboring compensating elements.

Any two neighboring compensating elements are connected to each other in a movable way by at least one foldable wire, with the foldable wire, which connects the neighboring compensating elements, bridging the gap positioned between neighboring compensating elements.

The term "wire" by definition comprises both metal wires and wires made of foldable plastic or synthetic fibers. This also includes coated wires.

The term "first implant" particularly signifies hip prostheses, knee prostheses or shoulder prosthesis, as well as femur, tibia and gamma nails or, in general, nails inserted into the bone marrow.

The oblong implant section of the implant is then, for example, the prosthesis shaft of a prosthesis, in particular the end section of a prosthesis shaft, or end sections in the case of bone nails.

The term "second implant" signifies an implant designed to be connected with the oblong implant section of the first implant, with the oblong implant section of the first implant being inserted into an e.g. essentially sheath-shaped intake device in the second implant and being fastened by means of a force-fit.

By attaching the compensating sleeve of this invention to the end section of the first implant, it is possible to compensate for a deficient form fit between the oblong section of the first implant and the second implant.

Depending on the extent of the structural differences, a force-fit connection of the first with the second implant can be achieved through the use of a compensating sleeve of this invention or, if a form-fit in fact exists, but the force-fit is not adequate, the secure mounting of the implant combination can be increased so that the required rotational stability is achieved.

A deficient fit is, among other things, attributable to the fact that the inside diameter of the sheath-like intake opening in the second implant is considerably larger than the outside diameter of the oblong implant section of the first implant, so that the two implants cannot be positively joined because of the size differences. There are also stability problems if the second implant has a cylindrical intake opening, but the existing interior prosthesis shaft tapers toward the end of the shaft.

By applying the compensating sleeve of this invention to the oblong implant section of the first implant it is possible to increase the outside diameter of the first implant, i.e. to thicken the end section by way of an increase in circumference, which can be limited circumferentially or locally, so that a proper fit for the cylindrical intake device in the second implant can be created.

In the case of profiled oblong implant sections of a first implant, there is primarily the problem of a low contact area size that can be used for a rotationally stable frictional connection in a sheath-like intake in a second implant. In this kind of situation, the groove profile can be filled through the use of the compensating sleeve of this invention over a defined section in the oblong end-region of the first implant, in that the compensating elements of the compensating sleeve of this invention engage one or several grooves in the implant. Depending upon the dimensions and the shape of the compensating elements (cross-sectional shape, radial extent), either just their outer surfaces facing the inner wall of the sheath-like intake device then constitute the contact surface for the rotationally stable frictional connection between the two implants or the existing contact surface of the oblong end region of the first implant is made larger by filling the grooves.

The compensating elements constituting the body of the sheath can be configured with two different basic designs.

In the first basic form, the compensating elements are planar, where the term "planar" signifies that the compensating element is flat and/or planar on both the side constituting a subsection of the sheath body and on the side assigned to the pass-through (facing the pass-through). A planar compensating element particularly has a polygonal cross-section passing from proximal to distal, preferably a rectangular, rhombic or trapezoidal cross-sectional shape. In other embodiments, the compensating element can also have triangular and polygonal cross-sectional shapes.

In the second basic form, the compensating elements are rod-shaped, where the term "rod-shaped" signifies that the compensating element has a convex protrusion at least on the inner side facing the path-through (pass-through side), with the protrusion advantageously extending along the entire length of the compensating element. A rod-shaped compensating element particularly signifies rods having a circular, ellipsoidal or semicircular cross-section passing from proximal to distal.

In a preferred embodiment, the cross-sectional shape and/or the diameter does not change over the entire length of the compensating element, but extends uniformly from one end to the other end of the compensating element.

The teaching of this invention also comprises empty compensating elements, whose cross-sectional profiles change over the length of the compensating element, in which, e.g., the cross-sectional profile transitions from a planar cross-sectional profile to a rod-shaped cross-sectional profile and vice versa.

The sheath body can, in particular, be composed of compensating elements of different designs and/or of different lengths, in that compensating elements located in the sheath body can vary from each other in their cross-sectional shape, the extent of the cross-sections or their length.

In a further embodiment, a compensating element can have a larger diameter in the distal boundary region of the sheath body than in its opposite proximal boundary region. The diameter of a compensating element advantageously increases uniformly over its length. The resulting change in size in the longitudinal direction of the sheath body can extend over the entire range, as all compensating elements of the sheath body exhibit a smaller diameter proximally than distally. But the change in size can also extend over just a partial segment of the sheath body, as only the compensating elements located there have a smaller diameter in the proximal range than in the distal range.

In the case of this embodiment, it is, for example, possible to compensate for a difference in fit between a first implant tapering toward the tip of the implant, e.g. the sheath of a hip prosthesis tapering in the distal direction, and a cylindrical implant-receiving device of a second implant.

In order to join the individual ring-shaped compensating elements so as to form the sheath body, neighboring compensating elements are interconnected by means of at least one folding wire so as to form a gap.

The basic structure of the compensating sleeve is recreated in the construction of a corset, where the compensating elements extending in the longitudinal direction of the sheath body are tied to each other by wires essentially extending in the longitudinal direction.

The gap width between two compensating elements can be decreased by folding, crumpling or buckling the wire, with the gap widths between any pair of adjacent compensating elements in the assembly of all compensating elements having differing dimensions. Two compensating elements in the sheath body assembly can thus be closer to each other than any two others.

By setting up sheath body sections wherein compensating elements are set up more far apart than in other regions of the sheath body, it is possible for edge regions or unprofiled regions in the oblong implant section to be encompassed, without the contact surface needed for a force-fit with the second implant being covered by a compensating element.

According to this invention, the wire connection between two compensating elements is not rigid, but bendable, so that while the position of each compensating element in the sheath body is defined, the compensating elements are movable within limits with respect to each other. The degree of motion is defined by the configuration of the connection of the foldable wire with the compensating element.

The compensating elements can, on the one hand, be mounted on the folding wire so that they can be shifted. To receive the wire, the compensating element is then preferably equipped with a drill hole or grommet through which the wire is passed.

In a preferred embodiment, the wire and compensating element are however firmly connected with each another. The fixed connection can, e.g., be made by welding or sticking together the wire and the compensating element. The shape flexibility of the sheath body is ensured herein by the gap widths between the compensating elements and by the use of a highly flexible wire.

The feed-through in the sheath body can be tailored to the dimensions and outside shape of the oblong implant section by way of the pronounced shape flexibility of the sheath body.

In case of a grooved profiling in the oblong implant section, the compensating elements in the sheath body can additionally be aligned with respect to each other so that one or more compensating elements of the sheath body fit in a groove of a groove profile in the first implant. The groove is thereby filled in its longitudinal direction over the length of the compensating sleeve, whereby the groove profile can be leveled in part or completely.

The wire bridging the gap is preferably aligned crosswise to the longitudinal axis of the sheath body, so that an inherently movable lattice structure is formed by the wiring of the compensating elements. The wire above all serves the purpose of holding the compensating elements within the sheath body in position in the assembly before the compensating sleeve is installed onto the oblong implant section.

In another embodiment, all compensating elements disposed in the sheath body are externally encompassed in a radially circumferential way by a folding wire, whereby all compensating elements disposed in the sheath body are connected with each other at the same height. Other ring-shaped wiring of the output elements can be present.

The compensating sleeve can be squeezed together via the application of force to the outside of one or several of the compensating elements constituting the sheath body, so that the sheath body deforms and/or the passage through the sheath body is compressed, at least in subsections.

A deformation of the sheath body can present itself as bending of one or several compensating elements in any possible direction. The term "deformation" also includes the compression of the sheath body in the radial direction, which leads to a constriction of the passage in the sheath body, at least over a part of the length of the compensating sleeve. A deformation of the sheath body also shows up as a change of the gap width between at least two compensating elements.

The compensating sleeve can be tailored to fit almost any outside shape of an oblong implant section and/or its surface profile by way of the deformation.

The radial extent of the oblong implant section can be increased in the region of this surface section by, for example, grouping compensating elements on a surface section in which the compensating elements can be placed on top of each other and/or next to each other with narrow gaps in between. A change in the shape of the cross-section of the oblong implant section of the first implant is thus subsequently and intentionally producible by sliding the compensating sleeve of this invention onto the oblong implant section over the contact region between the compensating sleeve and the implant section.

Because of the structural and functional characteristics of the compensating sleeve of this invention, it is possible to modify the basic shape of the oblong implant section such that an increase in rotational stability in the interconnection with the second implant is achieved, in that the differences in shape and form between the first and the second implant are compensated for.

The deformation of the sheath body is advantageously permanent, i.e. the deformed sheath body remains in its altered state after the end of the application of force.

A deformation of the sheath body consists of a kind of rearrangement where the gap between two neighboring compensating elements is decreased. The flexibility of the wire allows for a decrease of the gap widths. The wire, which can however be leveled due to its ability to fold by being mechanically folded in or back, bends up so that it does not negatively affect the installation of the second implant. The folding in of the wire also allows the compensating sleeve to be mounted firmly after it is slid over and fitted onto the oblong implant section, so that the risk of unwanted sliding off before the second implant is installed doesn't exist.

Depending upon the nature of the configuration, the compensating elements can be configured to be rigid for better access to the gap profile or for a more stable placement onto the top of the implant section.

The wiring of the compensating elements advantageously consists of wires with a diameter of 0.2-0.4 mm, in particular with a diameter of 0.3 mm. The folding wires are advantageously made of titanium or a surgical steel. A compensating element is preferably made of titanium, a titanium alloy, a surgical steel or a biocompatible plastic.

The invention is hereafter elucidated by means of example embodiments. The figures show:

FIG. 1: A side and cross-sectional view of an oblong implant section of a first implant, FIG. 2: A side view of an embodiment of a compensating sleeve of this invention, FIG. 3: A cross-sectional view of the embodiment in accordance with FIG. 2, FIG. 4: A side view of a compensating sleeve in accordance with FIG. 2 slid onto an oblong implant section in accordance with FIG. 1 and FIG. 5: A cross-sectional view of a compensating sleeve in accordance with FIG. 2 slid onto an oblong implant section in accordance with FIG. 1.

FIG. 1 shows both a side view and a cross-sectional view B-B of an oblong implant section 1 of a first implant 2. The first implant 2 shown is a straight bone nail with a groove profile 12 extending in the longitudinal direction. FIG. 1 shows the end region of the bone nail, which was, for instance, laid open surgically after a periprosthetic fracture. As the cross-sectional view B-B shows, the wavy groove profile 12 of the bone nail has broad troughs with short, pointed peaks.

For a force-fit connection with a second implant with a smooth-walled intake device into which the nail end 1 is to be introduced for an endoprosthetic extension, there is therefore only a very low contact area 13 available for power transmission, since contact can only be established between the wave crests and the wall of the intake device.

Figure 2:
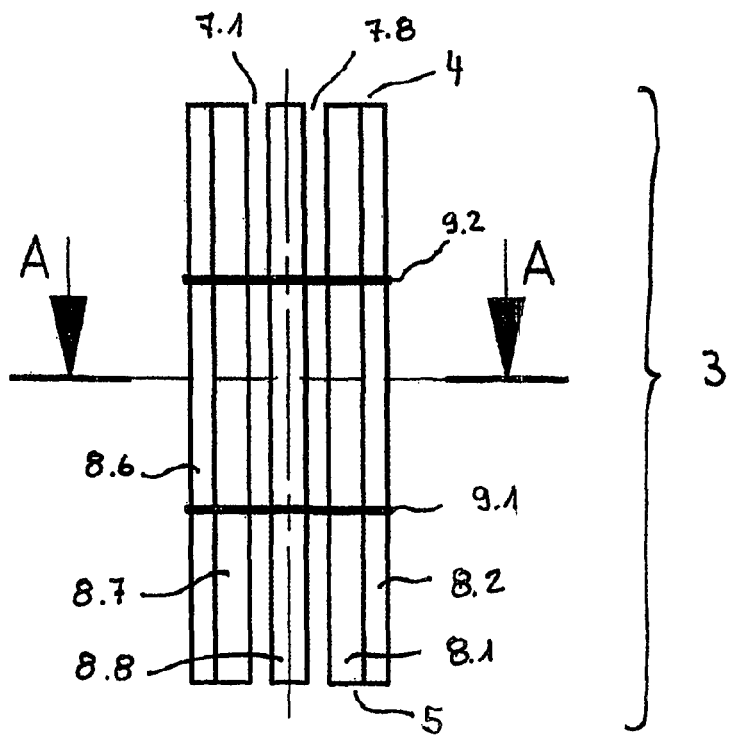
Figure 3:
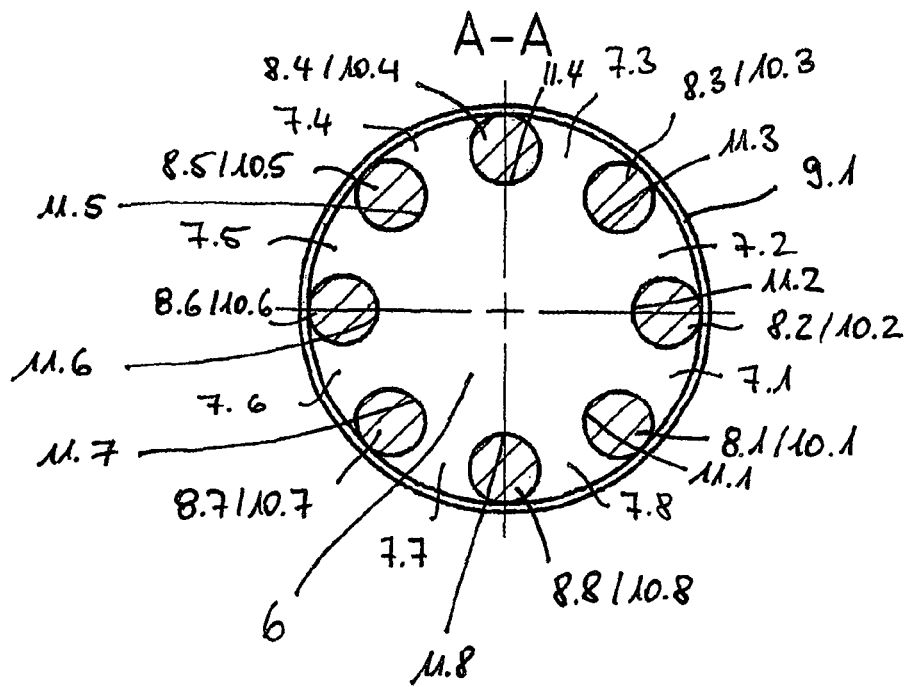

FIGS. 2 and 3 show an embodiment of the compensating sleeve of this invention. FIG. 3 portrays the cross-section A-A in accordance with FIG. 2.

The compensating sleeve is configured as a sheath with a sheath body 3 and with a lead-through 6 extending from the proximal 4 to the distal end 5 of the sheath body 3 so as to receive the oblong implant section 1 of the first implant 2.

The sheath body 3 consists of multiple ring-shaped rigid rods as compensating elements 8.1-8.8, which are connected to each other by two foldable wires 9.1 and 9.2 running around the outside of the sheath body, which are firmly attached to the outside of each rod 8.1-8.8. All of the rods 8.1-8.8 have the same length and circular cross-section 10.1-10.8 throughout, which are constant over the entire length of each rod 8.1-8.8. The rods 8.1-8.8 are installed at a distance from each other, so that the gap 7.1-7.8 is formed, with the gap width corresponding to the width of a wave crest of the groove profile 12. The wires 9.1 and 9.2 bridge all gaps 7.1-7.8 and thus also the crests of the groove profile 12.

The side of the rods 8.1-8.8 facing the lead-through 6 of the sheath body 3 constitutes the inside surface 11 of the sheath body 3.

Figure 4:
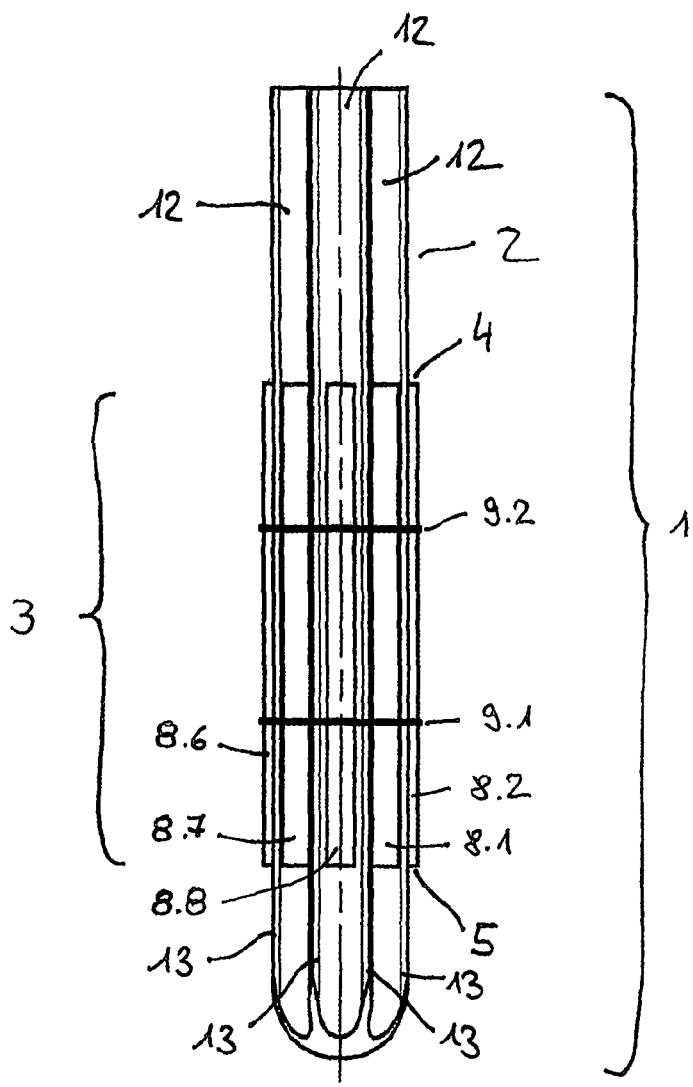
Figure 5:
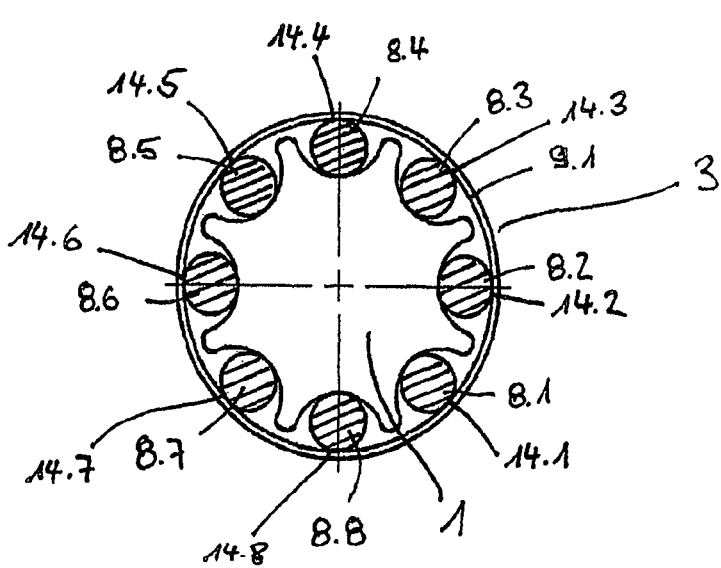

FIGS. 4 and 5 show a compensating sleeve that has been pushed onto the end section 2 of a bone nail 1. When the compensating sleeve is pushed on, one rod 8.1-8.8 of the sheath body 3 at a time engages a groove of the groove profile 12. The diameter of the rods 8.1-8.8 essentially corresponds to the depth of the grooves of the groove profile 12 in the oblong implant section 1, so that they essentially fill the groove when they engage with it (FIG. 5). The existing contact area 13 is nearly doubled by the exteriors 14.1-14.8 of the rods 8.1-8.8, whereby the rotational stability with respect to the second implant positioned within the domain of the compensating sleeve is increased, since the second implant not only rests on the wave crests of the groove profile 12 in a force-fit with the end section 2 of the nail but also on the outside surfaces 14.1-14.8 of the rods 8.1-8.8.

1 oblong implant section
2 first implant
3 sheath body
4 proximal end of the sheath body
5 distal end of the sheath body
6 continuous lead-through in the sheath body
7 a continuous gap from proximal to distal (7.1-7.8)
8 compensating elements (8.1-8.8)
9 folding wire (9.1-9.2)
10 circular cross-sectional shape of a compensating element
11 inside surface of the sheath body
12 groove profile in the oblong implant section of the first implant
13 contact surfaces for the force-fitted connection with the second implant
14 exterior of a compensating element (14.1-14.8)

The invention claimed is:

1. An implantable intramedullary compensating sleeve configured for installation around an oblong implant section of a prosthetic stem for the intramedullary treatment of a periprosthetic or interprosthetic fracture, the implantable intramedullary compensating sleeve consisting of:
   a sheath having a sheath body and a lead-through passage extending continuously from a proximal end of the sheath body to a distal end of the sheath body and configured to receive the oblong implant section of the prosthetic stem;
   wherein the sheath body is formed of separate and distinct compensating elements that are radially arranged in a ring and are aligned in a longitudinal direction of the sheath body; and
   wherein a continuous longitudinal gap extends between adjacent compensating elements and wherein the compensating elements are flexibly connected together by at least two discrete foldable wires that bridge over the continuous gaps,
   wherein the foldable wires are aligned so as to cross a longitudinal axis of the sheath body, and wherein the foldable wires wrap around the compensating elements and are firmly attached to an outside surface of each of the compensating elements,
   wherein the compensating elements are longitudinally-extending rigid rods,
   wherein the oblong implant section of the prosthetic stem comprises a grooved profile in cross-section,
   wherein when the compensating sleeve is slid on the oblong implant section of the prosthetic stem, a rod of the sheath body at a time engages a groove of the grooved profile of the oblong implant section of the prosthetic stem, and a diameter of the rods corresponds to a depth of the grooves of the grooved profile of the oblong implant section of the prosthetic stem, so that the rods substantially fill the grooves of the grooved profile of the oblong implant section of the prosthetic stem,
   wherein the sheath body is deformable by applying an external application of force on the outside surface of the compensating elements.

2. The implantable intramedullary compensating sleeve according to claim 1, wherein at least one of the compensating elements has at least one of a circular, ellipsoidal and semicircular cross-section passing uniformly from the proximal end to the distal end.

3. The implantable intramedullary compensating sleeve according to claim 1, wherein at least one of the compensating elements has a polygonal cross-section passing uniformly from the proximal end to the distal end.

4. The implantable intramedullary compensating sleeve according to claim 1, wherein each of the foldable wires has a diameter of 0.2-0.4 mm.

5. The implantable intramedullary compensating sleeve according to claim 1, wherein the continuous gap has a gap width that is reducible by mechanical folding of the foldable wires.

* * * * *